United States Patent [19]

Haga et al.

[11] 4,383,116

[45] May 10, 1983

[54] PROCESS FOR PRODUCING 4-BENZOYLPYRAZOLES

[75] Inventors: Takahiro Haga, Kusatsu; Tetsuji Nishikawa, Moriyama; Toshio Nakajima, Kusatsu; Kohji Minamida, Shiga; Masaru Maeda, Hikone, all of Japan

[73] Assignee: Ishihara Sangyo Kaisha Ltd., Osaka, Japan

[21] Appl. No.: 240,313

[22] Filed: Mar. 4, 1981

[30] Foreign Application Priority Data

Mar. 11, 1980 [JP] Japan .................................. 55-29829

[51] Int. Cl.$^3$ .......................................... C07D 231/20
[52] U.S. Cl. .................................................... 548/367
[58] Field of Search ........................................ 548/367

[56] References Cited

U.S. PATENT DOCUMENTS 3,939,203  2/1976  Mattison et al. ................... 564/266
4,070,536  1/1978  Konotsune et al. ................ 548/367
4,146,726  3/1979  Konotsune et al. ................ 548/367

OTHER PUBLICATIONS

Newman et al., J. Org. Chem., 1954, vol. 19, pp. 985–1002.
Wiley et al., Pyrazolones, Pyrazolidones and Derivatives, Interscience, NY, 1964, p. 22.

*Primary Examiner*—Henry R. Jiles
*Assistant Examiner*—Natalia Harkaway
*Attorney, Agent, or Firm*—Oblon, Fisher, Spivak, McClelland & Maier

[57] ABSTRACT

4-Benzoyl-5-hydroxypyrazoles useful as herbicidal active ingredients or their intermediate are produced by a condensation of a pyrazolone and a benzotrichloride followed by a hydrolysis reaction with industrial advantages.

8 Claims, No Drawings

PROCESS FOR PRODUCING 4-BENZOYLPYRAZOLES

BACKGROUND OF THE INVENTION

1. Field of the Invention

The present invention relates to a process for producing 4-benzoyl-5-hydroxypyrazoles or salts thereof (hereinafter referring to as 4-benzoylpyrazole derivatives) which are useful as active ingredients or intermediates or herbicides. More particularly, it relates to a process for producing 4-benzoylpyrazole derivatives by a condensation reaction of a pyrazolone derivative and a benzotrichloride derivative followed by a hydrolysis reaction.

2. Description of the Prior Arts

Heretofore, it has been known to produce 4-benzoylpyrazole derivatives by a reaction of a pyrazolone derivative with a benzoyl halide derivative in U.S. Pat. No. 4,063,925; and U.S. Pat. No. 4,008,200. In the processes, a 5-benzoyloxypryrazole derivative is produced as an intermediate and then, benzoyl group at 5-position of the intermediate is rearranged at 4-position to obtain 4-benzoylpyrazole derivative. Thus, the benzoyl halide derivatives used as the starting materials in the process have tearing properties that are the starting materials in the process have tearing properties that are easily effectively used. Moreover, the benzoyl halide derivative has been produced by a chlorination reaction of a side chain of toluene or a halogenotoluene followed by a hydrolysis reaction of the resulting product. The benzoyl halide derivative has been also produced by oxidizing toluene or halogenotoluene and reacting the resulting benzoic acid derivative with phosphorus trichloride, phosgen or thionyl chloride. The process comprises many steps and is expensive.

SUMMARY OF THE INVENTION

It is an object of the present invention to provide a process for producing 4-benzoylpyrazole derivatives.

It is another object of the present invention to provide a process for producing 4-benzoylpyrazole derivatives with industrial advantages by using economical starting materials in simple reactions.

The other objects of the present invention will be apparent by the following description.

In accordance with the present invention, it provides a process for producing a 4-benzoyl-5-hydroxypyrazole represented by the formula I;

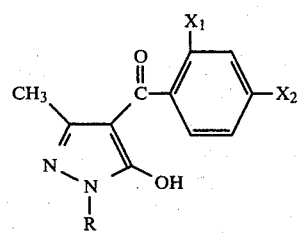

wherein R is a hydrogen atom or a lower alkyl group, $X_1$ and $X_2$ are respectively a hydrogen atom or a halogen atom, or salts of the pyrazoles which comprises a condensation reaction of a pyrazolone represented by the formula II;

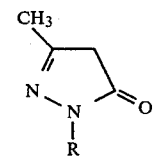

wherein R is the same defined as above, and a benzotrichloride represented by the formula III;

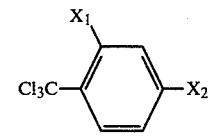

wherein $X_1$ and $X_2$ are the same defined as above, followed by a hydrolysis reaction.

DETAILED DESCRIPTION OF THE PREFERRED EMBODIMENTS

It has been found that 4-benzoylpyrazole derivatives as the object compounds are produced by directly condensing a pyrazolone derivative and a benzotrichloride derivative obtained by a chlorination of side chain of toluene or a halogenotoluene and then hydrolyzing the condensation product.

In the formulas I, II and III, the lower alkyl group as R can be methyl, ethyl, isopropyl or tert-butyl group; and the halogen atom as $X_1$ or $X_2$ can be chlorine, bromine or iodine atom, etc.

In accordance with the process of the present invention, economical starting materials can be used and 4-benzoylpyrazole derivatives as the object products can be easily produced in high yield with industrial advantages in comparison with the conventional processes.

In accordance with the process of the present invention, the condensation reaction of the pyrazolone derivative and the benzotrichloride derivative is usually carried out at a temperature ranging from minus 20° C. to 200° C. preferably 0° C. to 180° C. especially 60° to 150° C. and then, the hydrolysis reaction of the condensation product is carried out.

The condensation reaction mixture is usually hydrolyzed by adding water to it without discharging it from the reaction system.

The condensation reaction is usually carried out by using 0.7 to 1 mole preferably about equimole of the benzotrichloride derivative per 1 mole of the pyrazolone derivative in the presence of an acid acceptor or a catalyst.

The acid acceptors can be alkaline materials such as tert-amines such as pyridine and triethylamine; and hydroxides, carbonates and bicarbonates of alkali metal or alkaline earth metal.

The catalysts can be aluminum chloride, zinc chloride, iron chloride. It is optimum to use aluminum chloride.

An amount of the acid acceptor or the catalyst is usually in a range of 1 to 5 mole preferably 1 to 3 mole per 1 mole of the pyrazolone derivative.

The condensation reaction is usually carried out in the presence of a solvent. When the condensation reaction is carried out in the presence of the acid acceptor, the solvents are preferably selected from water; alcohols such as methanol and ethanol; ethers such as diethyl ether and diisopropyl ether; cyclic ethers such as tetrahydrofurane and dioxane; aromatic hydrocarbones such as benzene and toluene; halohydrocarbons such as methylene chloride, dichloroethane, tetrachloroethane and m-dichlorobenzene; ketones such as acetone and methylethyl ketone; amides such as dimethylformamide and dimethylacetamide; aprotonic polar solvents such as dimethylsulfoxide and sulpholan and carbon disulfide etc.

When the condensation reaction is carried out in the presence of the catalyst, the solvents are preferably selected from the above-mentioned halohydrocarbons and carbon disulfide etc.

The hydrolysis reaction in the process of the present invention is usually carried out by adding water to the reaction product obtained by the condensation reaction. For example, after confirming the completion of the condensation reaction, the hydrolysis reaction of the reaction product is usually carried out without discharging the reaction mixture at a temperature ranging from 0° C. to 150° C. preferably room temperature to 100° C.

When the condensation reaction is carried out in the presence of the acid acceptor, the hydrolysis reaction is usually carried out by adding an alcoholic solution or aqueous solution containing an alkaline material at a molar ratio of 2 to 4 preferably about 3 based on the condensation reaction product.

When the condensation reaction is carried out in the presence of the catalyst, the hydrolysis reaction is usually carried out by adding an aqueous solution of a mineral acid such as hydrochloric acid, sulfuric acid etc. at a molar ratio of 3 to 10 preferably 4 to 6 based on the condensation reaction product.

Reaction times for the condensation reaction and the hydrolysis reaction of the present invention are not critical and selected depending upon the other conditions of the reactions and are respectively usually in a range of 0.2 to 10 hours. After the completion of the reaction, the reaction mixture is treated by the conventional separation and purification such as a solvent extraction, an acid treatment, and a distillation to obtain 4-benzoylpyrazole derivative as the object product.

The present invention will be further illustrated by certain examples and references which are provided for purposes of illustration only and are not intended to be limiting the present invention.

EXAMPLE 1

A mixture of 1 g. of 1,3-dimethyl-5-pyrazolone and 2 g. of 2,4-dichlorobenzotrichloride was heated at 140° C. for 3 hours with stirring to perform a condensation reaction. After the reaction, the reaction mixture was cooled to 70° C. A solution of 1.1 g. of potassium hydroxide in 10 ml. of 50% ethanol-water was added dropwise to the reaction mixture and the mixture was stirred for 1 hour to perform a hydrolysis reaction. The reaction mixture was cooled to the room temperature and was acidified with hydrochloric acid. The reaction product was extracted with methylene chloride and dehydrated over anhydrous sodium sulfate to obtain 2.4 g. of a crude crystal.

According to a liquid chromatography analysis, it contained 22% of 1,3-dimethyl-4-(2,4-dichlorobenzoyl)-5-hydroxypyrazole as the object product.

EXAMPLE 2

A mixture of 0.5 g. of 1,3-dimethyl-5-pyrazolone, 1.0 g. of 2,4-dichlorobenzotrichloride and 0.4 ml. of pyridine was heated at 120° C. for 4 hours with stirring to perform a condensation reaction. A solution of 0.7 g. of potassium hydroxide in 5 ml. of water and 5 ml. of ethanol was added to the reaction mixture at 70° C. with stirring and the mixture was stirred for 1 hour. The reaction mixture was cooled to the room temperature and was admixed with 20 ml. of methylene chloride with thoroughly stirring. The water phase was separated and acidified to be pH of 1 with conc. hydrochloric acid. The reaction product was extracted from the water phase with methylene chloride. The extract was washed with water and dehydrated over anhydrous sodium sulfate and the solvent was distilled off to obtain 0.65 g. of 1,3-dimethyl-4-(2,4-dichlorobenzoyl)-5-hydroxypyrazole.

EXAMPLE 3

Into 10 ml. of water, 2 g. of 1,3-dimethyl-5-pyrazolone was dissolved and then, 3.5 g. of benzotrichloride was added at the room temperature with stirring. A solution of 5 g. of potassium hydroxide in 15 ml. of 50% ethanol-water was added to the reaction mixture with stirring and the mixture was further stirred at 80° C. for 30 minutes to perform a condensation reaction and a hydrolysis reaction. The reaction mixture was treated for purification as set forth in Example 2 to obtain 2.5 g. of 1,3-dimethyl-4-benzoyl-5-hydroxypyrazole.

EXAMPLE 4

In accordance with the process of Example 3 except using 2 g. of 1-isopropyl-3-methyl-5-pyrazolone, 3.9 g. of p-bromobenzotrichloride and 4 g. of potassium hydroxide, the condensation reaction, the hydrolysis reaction and the purification were carried out to obtain 2.2 g. of 1-isopropyl-3-methyl-4-(4-bromobenzoyl)-5-hydroxypyrazole.

EXAMPLE 5

Into 10 ml. of water, 1 g. of 3-methyl-5-pyrazolone was suspended and then 2 g. of benzotrichloride was added to the suspension at the room temperature. A solution of 2.9 g. of potassium hydroxide in 15 ml. of 50% ethanol-water was added to the reaction mixture with stirring and the mixture was stirred at 90° C. for 1 hour to perform a condensation reaction and a hydrolysis reaction.

The reaction mixture was cooled to the room temperature and was acidified with conc. hydrochloric acid. The reaction product was extracted with methylene chloride and the extract was dehydrated over anhydrous sodium sulfate and the solvent was distilled off to obtain 1.7 g. of a crude crystal. According to a liquid chromatography analysis, it contained 38% of 3-methyl-4-benzoyl-5-pyrazolone (m.p.: 258°–266° C.).

EXAMPLE 6

Into 15 ml. of dichloroethane, 2.4 g. of 2,4-dichlorobenzotrichloride was dissolved and then, 1.3 g. of aluminum chloride was added and 1.0 g. of 1,3-dimethyl-5-pyrazolone was further added. The mixture was refluxed for 1.5 hours to perform a condensation reaction. The reaction mixture was cooled and 30 ml. of 6 N-HCl was added dropwise to the reaction mixture. The mixture was refluxed for 2 hours to perform a hydrolysis reaction. The reaction mixture was cooled to perform a phase separation. The reaction product was extracted with methylene chloride and the extract phase was mixed with a saturated aqueous solution of sodium bicarbonate to extract the reaction product. The aqueous solution was acidified with hydrochloric acid and the reaction product was further extracted with methylene chloride. The extract was dehydrated over anhydrous sodium sulfate and the solvent was distilled off to obtain 2.4 g. of 1,3-dimethyl-4-(2,4-dichlorobenzoyl)-5-hydroxypyrazole.

EXAMPLE 7

A mixture of 1.36 g. of 1,3-dimethyl-5-pyrazolone, 3.1 g. of 2,4-dichlorobenzotrichloride and 3.1 g. of anhydrous aluminum chloride was melted and heated at 100° C. for 1 hour to perform a condensation reaction. The reaction mixture was cooled and 10 ml. of dichloroethane was added to the reaction mixture and then 5 ml. of water was added dropwise under cooling with water and then 15 ml. of conc. hydrochloric acid was added dropwise and the mixture was heated at 70° C. for 2 hours to perform a hydrolysis reaction. The reaction mixture was cooled and the organic phase was separated. The reaction product was extracted with 3% aqueous solution of potassium hydroxide. The aqueous solution was acidified and the reaction product was further extracted with methylene chloride. The extract was washed with water and dehydrated and the solvent was distilled off to obtain 3.2 g. of 1,3-dimethyl-4-(2,4-dichlorobenzoyl)-5-hydroxypyrazole.

EXAMPLE 8

Into 8 ml. of dichloroethane, 1.32 g. of 1,3-dimethyl-5-pyrazolone was dissolved and then, 3.1 g. of anhydrous aluminum chloride was added to the solution and the mixture was heated at 70° C. with stirring. A solution of 3 g. of 2,4-dichlorobenzotrichloride in 5 ml. of dichloroethane was added dropwise and the mixture was refluxed for 1 hour to perform a condensation reaction. The reaction mixture was cooled and then, 15 ml. of conc. hydrochloric acid was added dropwise and the mixture was heated at 70° C. for 2 hours to perform a hydrolysis reaction. The organic phase was separated and washed with water and dehydrated and the solvent was distilled off to obtain 3.2 g. of 1,3-dimethyl-4-(2,4-dichlorobenzoyl)-5-hydroxypyrazole.

In accordance with the above-mentioned process, except using carbon disulfide instead of dichloroethane, the condensation reaction and the hydrolysis reaction were carried out. The same result was attained.

EXAMPLE 9

Into 10 ml. of dichloroethane, 1.11 g. of 3-methyl-5-pyrazolone was dissolved and then 3.1 g. of anhydrous aluminum chloride was added. A solution of 3 g. of 2,4-dichlorobenzotrichloride in 5 ml. of dichloroethane was added dropwise to the mixture with stirring. The mixture was refluxed for 1 hour to perform a condensation reaction. The reaction mixture was cooled and 15 ml. of conc. hydrochloric acid was added dropwise and the mixture was heated at 70° C. for 2 hours to perform a hydrolysis reaction. After cooling the reaction mixture, the solid matter was separated by a filtration and was washed with water and dried to obtain 3.0 g. of 3-methyl-4-(2,4-dichlorobenzoyl)-5-hydroxypyrazole.

EXAMPLE 10

A mixture of 1.7 g. of benzotrichloride and 2.5 g. of anhydrous zinc chloride was admixed with 1.0 g. of 1,3-dimethyl-5-pyrazolone and the mixture was stirred at room temperature and then, was heated at 200° C. for 2 hours to perform a condensation reaction. The reaction mixture was acidified with 15 ml. of conc. hydrochloric acid and the mixture was heated at 70° C. for 2 hours to perform a hydrolysis reaction. In accordance with the process of Example 8, the reaction product was purified to obtain 1.1 g. of 1,3 dimethyl-4-benzoyl-5-hydroxypyrazole.

EXAMPLE 11

A mixture of 2.8 g. of 4-chlorobenzotrichloride and 10 ml. of dichloroethane was admixed with 2.6 g. of anhydrous ferric chloride and 1.36 g. of 1,3-dimethyl-5-pyrazolone and the mixture was stirred at room temperature and then refluxed for 2 hours to perform a condensation reaction. The reaction mixture was acidified with 15 ml. of conc. hydrochloric acid, and heated at 70° C. for 2 hours to perform a hydrolysis reaction.

In accordance with the process of Example 8, the reaction product was purified to obtain 0.9 g. of 1,3-dimethyl-4-(4-chlorobenzoyl)-5-hydroxypyrazole.

We claim:

1. A process for producing a 4-benzoyl-5-hydroxypyrazole represented by the formula

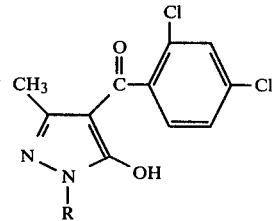

wherein R is a hydrogen atom or a lower alkyl group, which comprises a condensation reaction of a pyrazolone represented by the formula

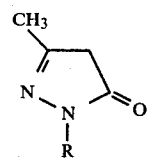

wherein R is the same defined as above, and a benzotrichloride represented by the formula

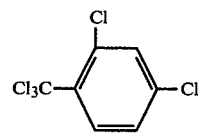

followed by a hydrolysis reaction.

2. The process according to claim 1 wherein the condensation reaction is carried out in the presence of an acid acceptor or a catalyst.

3. The process according to claim 1 for producing a 1,3-dimethyl or 3-methyl-4-(2,4-dichlorobenzoyl)-5-hydroxypyrazole which comprises a condensation reaction of a 1,3-dimethyl or 3-methyl-5-pyrazolone and a 2,4-dichlorobenzotrichloride followed by a hydrolysis reaction.

4. The process according to claim 3 wherein the condensation reaction is carried out in the presence of an acid acceptor or a catalyst.

5. The process according to claim 3 wherein the condensation reaction is carried out in the presence of aluminum chloride.

6. The process according to claim 3 wherein the condensation reaction is carried out in the presence of a solvent of a halogenated hydrocarbon or carbon disulfide and aluminum chloride.

7. The process according to claim 3 wherein the condensation reaction is carried out in the presence of an acid acceptor and the hydrolysis reaction is carried out by using an aqueous alcohol solution containing an alkaline material.

8. The process according to claim 3 wherein the condensation reaction is carried out in the presence of a catalyst and the hydrolysis reaction is carried out by using an aqueous acid solution.

* * * * *